(12) United States Patent
Fehr

(10) Patent No.: US 7,253,141 B2
(45) Date of Patent: Aug. 7, 2007

(54) MUSK ODORANT COMPOUNDS

(75) Inventor: Charles Fehr, Versoix (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 11/413,456

(22) Filed: Apr. 27, 2006

(65) Prior Publication Data

US 2006/0211598 A1    Sep. 21, 2006

Related U.S. Application Data

(63) Continuation of application No. PCT/IB2004/003628, filed on Nov. 4, 2004.

(30) Foreign Application Priority Data

Nov. 28, 2003 (WO) .................. PCT/IB03/05630

(51) Int. Cl.
    *A61Q 99/00* (2006.01)
    *A61K 8/35* (2006.01)
    *A61K 8/49* (2006.01)
    *C07C 49/637* (2006.01)
    *C07D 303/32* (2006.01)

(52) U.S. Cl. .................. 512/13; 512/15; 549/545; 568/374

(58) Field of Classification Search ............... 549/545; 568/374; 512/13, 15
See application file for complete search history.

(56) References Cited

U.S. PATENT DOCUMENTS

| 3,773,836 A | | 11/1973 | Hall .................. 260/586 R |
| 3,847,993 A | * | 11/1974 | Hall et al. ............ 568/360 |
| 3,927,083 A | * | 12/1975 | Hall et al. ............ 512/13 |
| 5,077,273 A | | 12/1991 | Sprecker et al. ........ 512/13 |
| 5,114,915 A | | 5/1992 | Fehr et al. ............ 512/15 |
| 5,163,453 A | * | 11/1992 | Bachmann et al. ....... 131/276 |
| 5,324,875 A | | 6/1994 | Fehr et al. ............ 585/26 |

FOREIGN PATENT DOCUMENTS

| EP | 0 405 427 B1 | 1/1991 |
| EP | 0 465 936 B1 | 1/1992 |
| EP | 0 664 286 B1 | 7/1995 |

OTHER PUBLICATIONS

Fehr et al, Helvetica Chimica Acta, vol. 85, p.533-543 (Feb. 2002).*

* cited by examiner

*Primary Examiner*—Bernard Dentz
(74) *Attorney, Agent, or Firm*—Winston & Strawn LLP

(57) ABSTRACT

The present invention discloses keto derivatives of 5,5,6,7,8,8-hexamethyl-hexahydronaphthalene or keto-epoxy derivatives of 5,5,6,7,8,8-hexamethyl-octahydronaphthalene which are useful perfuming ingredients having a musky-earthy character.

11 Claims, No Drawings

MUSK ODORANT COMPOUNDS

CROSS-REFERENCE TO RELATED APPLICATIONS

This application is a continuation of International application PCT/IB2004/003628 filed on Nov. 4, 2004, the entire content of which is expressly incorporated herein by reference thereto.

TECHNICAL FIELD

The present invention relates to the field of perfumery. More particularly, it concerns a keto derivative of 5,5,6,7,8,8-hexamethyl-hexahydronaphthalene or a keto-epoxy derivative of 5,5,6,7,8,8-hexamethyl-octahydronaphthalene, as defined in formula (I) or (I') disclosed further below.

BACKGROUND

Compounds having musky odor notes and capable of imparting interesting olfactif effect to a composition are of high interest for the perfumery industry, especially if they possess a well balanced earthy note.

To the best of our knowledge, the compounds belonging to formula (I) or (I'), as defined below, are unknown.

The prior art discloses few examples of useful perfuming ingredients having a structural similarity with the invention's compounds. However the prior art compounds differ significantly from the ones of formula (I) or (I') by their structure and by their organoleptic properties, so that they cannot be considered as anticipating the embodiment of the present invention.

As examples of the prior art compounds one may cite the ones cited in EP 405427 or EP 664286, which possess an aromatic ring, or yet the ones cited in U.S. Pat. No. 3,773,836, which are derivatives of indanone.

SUMMARY OF THE INVENTION

The present invention relates about a keto derivative of 5,5,6,7,8,8-hexamethyl-hexahydronaphthalene or a keto-epoxy derivative of 5,5,6,7,8,8-hexamethyl-octahydronaphthalene, as defined further below, as well as the use of the compounds in perfumery. The invention concerns also the compositions or articles associated with the compound.

DETAILED DESCRIPTION OF THE PREFERRED EMBODIMENTS

Surprisingly, we have now established that a compound of formula (I) or of formula (I')

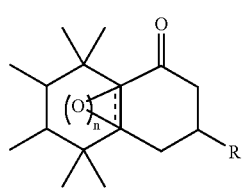

(I)

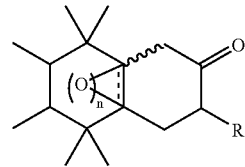

(I')

wherein R represents a hydrogen atom or a methyl group, and
  a) in formula (I):
    n is 1 and the dotted line represents a single bond; or
    n is 0 and the dotted line represents a double bond; or
  b) in formula (I'):
    n is 0, the wavy line indicates a double bond and the dotted line a single bond; or
    n is 0, the wavy line indicates a single bond, the dotted line a double bond; or
    n is 1, the wavy line indicates a single bond, the dotted line a single bond;

possesses surprising odor properties, of the musky-earthy type, which have been found to be particularly useful and appreciated for the preparation of perfumes, perfuming compositions and perfumed products.

Amongst the compounds of formula (I) or (I'), those of formula (II) or (II')

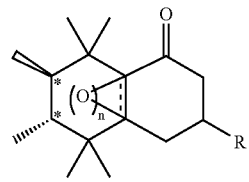

(II)

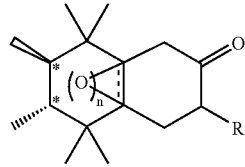

(II')

wherein the two methyl groups bonded to the carbons marked by an asterisk possess a trans configuration, and R, n and the dotted line have the meaning indicated in formula (I);

represent a particularly appreciated embodiment of the invention, due to their remarkable fragrance and odor substantivity or tenacity.

Amongst the compounds responding to the formulae cited above, one may cite in particular, and as non-limiting example, (6RS,7RS)-5,5,6,7,8,8-hexamethyl-3,4,5,6,7,8-hexahydronaphthalen-1(2H)-one which possesses a very strong and complex odor profile wherein several nuances are present with the musky-earthy notes typical of the invention's compounds. Indeed its odor is characterized by an excellent musky and earthy-cellar note, recalling surprisingly the odor of TONALIDE® (5,6,7,8-tetrahydro-3,5,5,6,8,8-hexamethyl-2-naphthyl)-1-ethanone; origin: PFW, Holland), associated with bottom notes of the fruity-quince, nitro-musk type as well as a slightly animal aspect. The presence of nitro-musk bottom note is quite surprising for a compound which does not possess an aromatic ring. Furthermore, it can be added the woody notes, typical of a musk like CASHMERAN® (1,2,3,5,6,7-hexahydro-1,1,2,3,3-pentamethyl-4-indenon; origin: I.F.F., USA), are very weak, and contribute in a minimal part to the characteristic odor of (6RS,7RS)-5,5,6,7,8,8-hexamethyl-3,4,5,6,7,8-hexahydronaphthalen-1(2H)-one. The overall fragrance is also highly substantive on a large number of surface and especially on skin or on fabrics.

In fact, due to the earthy note and the slightly animal aspect, one may say that the fragrance of (6RS,7RS)-5,5,6,7,8,8-hexamethyl-3,4,5,6,7,8-hexahydronaphthalen-1(2H)-one is reminding of the odor of TONALIDE® with in addition a fruity and nitro-musk character as well as a slight animal connotation similar to the one of CASHMERAN®.

Another example of the invention's compounds is (6RS,7RS)-3,5,5,6,7,8,8-heptamethyl-3,4,5,6,7,8-hexahydronaphthalen-1(2H)-one which possesses an odor profile quite similar to that of the compound mentioned above, but it differentiates from the latter by the presence of a note of the Ambrette type and a stronger earthy note, which recall even more the odor of TONALIDE® or even that of VULCANOLIDE® (trans-5,6,7,8-tetrahydro -3,5,5,6,7,8,8-heptamethyl-2-naphthalenecarbaldehyde; origin: Firmenich, Switzerland).

A further example of a compound of formula (II) is (4aRS,6RS,7RS,8aSR) -5,5,6,7,8,8-hexamethylhexahydro-4a,8a-epoxynaphthalen-1(2H)-one. The compound has a fragrance characterized by musky-earthy and nitro-musk notes in association with pine, powdery and sweet undernotes. However, this invention's compound differs from the ones mentioned above by having an earthy connotation weaker than the one of the two compounds mentioned above. The whole organoleptic profile of (4aRS,6RS,7RS,8aSR)-5,5,6,7,8,8-hexamethylhexahydro-4a,8a-epoxynaphthalen-1(2H)-one is in the direction of the odor of GALOXILIDE® (another aromatic musk, which is frequently described as having a sweet-musky odor).

The other isomer of the above-mentioned epoxide, namely (4aSR,6RS,7RS,8aRS) -5,5,6,7,8,8-hexamethylhexahydro-4a,8a-epoxynaphthalen-1(2H)-one, possesses a fragrance which is more musky but weaker than the one of its isomer.

Amongst the compounds of formula (I') or (II') one may cite, as non-limiting examples, (6RS,7RS)-5,5,6,7,8,8-hexamethyl-4,4a,5,6,7,8-hexahydronaphthalen-2(3H)-one which, in addition to the usual musky and earthy character, possesses also a slightly woody-pear bottom note.

Furthermore, one may also mention 3,5,5,6,7,8,8-heptamethyl-3,4,5,6,7,8-hexahydronaphthalen-2(1 H)-one which possesses a nice musky, dry and powdery note associated with an earthy and slightly woody connotation. The overall odor of this compound is recalling the one of TONALIDE® and GALAXOLIDE®.

Finally, the odor of (6RS,7RS)-5,5,6,7,8,8-hexamethyl-3,4,5,6,7,8-hexahydro -naphthalen-2(1H)-one is characterized by a strong and well-balanced earthy musky, musk-ambrette type note having also a powdery and ambrette's seeds undernote. The whole odor can be also described as a musky-earthy type in the direction of GALAXOLIDE® and CELESTOLIDE® (1-(6-tert-butyl-1,1-dimethyl-4-indanyl)-1-ethanone; origin: I.F.F., USA).

Therefore, the invention's compounds, despite having a structural similarity to that of the compounds disclosed in U.S. Pat. No. 3,773,836, distinguish from the latter by a quite different organoleptic profile. Indeed, the musk note of the invention's compounds, to the contrary of those of U.S. Pat. No. 3,773,836, is characterized by the presence of a more or less pronounced earthy note wherein the woody note is fairly absent, or quite weak and of the pine type, rather than of the "precious wood" type. In fact the odor profile of the invention's compounds is more in the direction of the TONALIDE® or GALAXOLIDE® profile, rather than in the direction of CASHMERAN®.

According to a particularly appreciated embodiment of the invention, (6RS,7RS) -5,5,6,7,8,8-hexamethyl-3,4,5,6,7,8-hexahydronaphthalen-1(2H)-one will be used in perfumery application in a preferential manner.

The invention's compounds, in a general manner, can be obtained using 5,6,7,8-tetrahydro-3,5,5,6,7,8,8-heptamethyl-naphthalene, in the form of the cis or trans isomers or a mixture thereof, as starting material. The heptamethyl-naphthalene derivative can be optionally demethylated in the position 3, into 5,6,7,8-tetrahydro-5,5,6,7,8,8-hexamethyl-naphthalene, for example using a method as described in the examples. Both 5,6,7,8-tetrahydro-3,5,5,6,7,8,8-heptamethyl-naphthalene and 5,6,7,8-tetrahydro-5,5,6,7,8,8-hexamethyl-naphthalene can subsequently be partially reduced using a Birch type reaction or a partial hydrogenation, into the desired hydronaphthalene derivative. The latter is consequently oxidized into an epoxide, which is rearranged into the corresponding ketone, or is oxidized in an allylic position to provide a ketone, which is optionally further epoxidized.

Typical examples of such synthetic schemes are described in the examples further below.

As the invention's compounds are valuable perfuming ingredients, the invention concerns also the use of the compounds as perfuming ingredients. In other words it concerns a method to confer, enhance, improve or modify the odor properties of a perfuming composition or of a perfumed article, which method comprises adding to the composition or article an effective amount of at least a compound of formula (I) and/or (I'). By "use of a compound of formula (I) and/or (I')" it has to be understood here also the use of any composition containing a compound (I) and/or (I') and which can be advantageously employed in perfumery as active ingredients.

The compositions, which in fact can be advantageously employed as perfuming ingredient, are also an embodiment of the present invention.

Therefore, another embodiment of the present invention is a perfuming composition comprising:

i) as perfuming ingredient, at least one invention's compound, as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. The carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials, for examples, may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

Generally speaking, by "perfumery base" we mean here a composition comprising at least one perfuming co-ingredient.

The perfuming co-ingredient is not of the formula (I) and/or (I'). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitrites, terpene hydrocarbons, nitrogenous or sulphurous heterocyclic compounds and essential oils, and the perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that the co-ingredients may also be compounds known to release in a controlled manner various types of perfuming compounds.

For the compositions which comprise both a perfumery carrier and a perfumery base, other suitable perfumery carrier, than those previously specified, can be also ethanol, water/ethanol mixtures, limonene or other terpenes, isoparaffins such as those known under the trademark ISOPAR® (origin: Exxon Chemical) or glycol ethers and glycol ether esters such as those known under the trademark DOWANOL® (origin: Dow Chemical Company).

Generally speaking, by "perfumery adjuvant" we mean here an ingredient capable of imparting additional added benefit such as a color, a particular light resistance, chemical stability and etc. A detailed description of the nature and type of adjuvant commonly used in perfuming bases cannot be exhaustive, but it has to be mentioned that the ingredients are well known to a person skilled in the art.

An invention's composition consisting of at least one invention's compound and at least one perfumery carrier represents a particular embodiment of the invention as well as a perfuming composition comprising at least one invention's compound, at least one perfumery carrier, at least one perfumery base, and optionally at least one perfumery adjuvant.

It is useful to mention here that the possibility to have, in the compositions mentioned above, more than one compound of formula (I) and/or (I') is important as it enables the perfumer to prepare accords, perfumes, possessing the odor tonality of various compounds of the invention, creating thus new tools for their work.

Preferably, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odor of a consumer product into which the compound (I) is added. Consequently, a perfumed article comprising:

i) as perfuming ingredient, at least one invention's compound, as defined above; and ii) a consumer product base, is also an embodiment of the present invention.

For the sake of clarity, it has to be mentioned that, by "consumer product base" we mean here a consumer product, which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of the product.

Examples of suitable consumer product bases include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.5% to 50% by weight, or even more, of the compounds of the invention based on the weight of the composition into which they are incorporated. Concentrations lower than these, such as in the order of 0.05% to 5% by weight, can be used when these compounds are incorporated into perfumed articles.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and 90 or 100 MHz for $^{13}C$, the chemical shifts δ are indicated in ppm with respect to the TMS as standard, the coupling constants J are expressed in Hz.

Example 1

Synthesis of (6RS,7RS)-3,5,5,6,7,8,8-heptamethyl-3,4,5,6,7,8-hexahydronaphthalen-1(2H)-one a) Synthesis of trans-1,2,3,4-tetrahydro-1,1,2,3,4,4,6-heptamethylnaphthalene A mixture of VULCANOLIDE® (50.0 g; 193 mmol) and 10% Pd/C (500 mg; 1% by weight) under $N_2$ was heated at 170° C. for 24 hours in a two-necked flask fitted with a condenser. Then, another portion of 10% Pd/C (500 mg) was added and heating continued for 16 hours. The cooled solid reaction mixture was dissolved in ether, filtered on Celite®, concentrated and bulb-to-bulb distilled (0.01 mbar; 100-125° C.) to afford 39.06 g of the desired heptamethylnaphthalene (yield=88%).

$^1$H-NMR: 0.94-0.98 (d, 6H, J=7 Hz), 1.08 (s, 3H), 1.09 (s, 3H), 1.30 (s, 3H), 1.31 (s, 3H), 1.55-1.62 (m, 2H), 2.31 (s, 3H), 6.93-6.99 (d, 1H, J=7.5 Hz), 7.16 (s, 1H), 7.22-7.28 (d, 1H, J=7.5 Hz). $^{13}$C-NMR: 145.43 (s), 142.64 (s), 134.52 (s), 127.59 (d), 127.07 (d), 126.49 (d), 39.37 (d), 37.77 (s), 37.54 (s), 29.60 (q), 29.51 (q), 25.62 (q), 25.58 (q), 21.11 (q), 13.85 (q), 13.82 (q).

b) Synthesis of trans-1,2,3,4,5,8-hexahydro-1,1,2,3,4,4,6-heptamethylnaphthalene Methylamine (200 ml, Fluka, cylinder) was condensed in a 5-neck flask fitted with a $CO_2$-condenser and an argon line. The temperature was allowed to reach −12° C. and a solution of the compound obtained under a) (15.0 g; 65.1 mmol) in THF (40 ml) and EtOH (11.4 ml, 9.0 g; 196 mmol) was added. To this magnetically stirred solution was added portionwise lithium (1.35 g; 196 mmol) over 2 hours. After complete addition, methylamine was allowed to evaporate overnight. Saturated aqueous $NH_4Cl$ was added and the products extracted with ether. The organic phase was washed with water, then saturated aqueous NaCl, dried ($Na_2SO_4$) and evaporated (18.2 g). Bulb-to-bulb distillation (0.01 mbar, 120° C.) afforded 14.49 g of the desired compound (65% by GC) and of trans-1,2,3,4,5,6,7,8-octahydro-1,1,2,3,4,4,6-heptamethylnaphthalene (25% by GC). The extrapolated yield for the title compound is 62% (9.42 g).

MS: 232 (20), 217 (10), 133 (82), 119 (100), 105 (31), 91 (35), 55 (32), 41 (42).

c) Synthesis of trans-1,2,3,4,5,6,7,8-octahydro-1,1,2,3,4,4,6-heptamethylnaphthalene It was proceeded as for example 1.b), but after stirring the reaction mixture (containing 3 equiv. of Li) for 1 h, another portion of Li (3 equiv.) and EtOH (3 equiv.) was added and the stirring was continued at −10° C. for 1 h. Starting from trans-1,2,3,4-tetrahydro-1,1,2,3,4,4,6-heptamethylnaphthalene (2.00 g; 8.70 mmol), 1.93 g of desired octahydroheptamethylnaphthalene (85% pure; 81% yield) were obtained after bulb-to-bulb distillation.

MS: 234 (20), 219 (100), 177 (26), 163 (49), 123 (29), 121 (27), 107 (22), 91 (24), 55 (34), 41 (41).

d) Synthesis of (6RS,7RS)-3,5,5,6,7,8,8-heptamethyl-3,4,5,6,7,8-hexahydronaphthalen-1(2H)-one A suspension of $CrO_3$ (12.8 g; 128 mmol) in $CH_2Cl_2$ (186 ml) was cooled at −23° C. and treated at once with 3,5-dimethylpyrazole (DMP) (12.29 g; 128 mmol). After 20 minutes, the solution was treated dropwise (over 20 minutes) with a solution of the compound obtained under c) (1.50 g; 85% pure; 5.51 mmol) in $CH_2Cl_2$ (22 ml). After stirring at −20° C. for 2.5 hours, 6 M aqueous NaOH (25 ml) was added and the solution stirred at 0° C. for 30 min. More water was then added and the product extracted. The $CH_2Cl_2$ phase was washed with 5% aqueous HCl and brine (3 times), and finally dried ($Na_2SO_4$) and evaporated. The crude product (2.45 g) was bulb-to-bulb distilled (0.01 mbar; 150-160° C.) to afford 1.33 g of a distillate. The latter was further purified by a flash chromatography ($SiO_2$, using cyclohexane/ethylacetate 98:2) which afforded 569 mg of the desired ketone (ca. 90% pure; yield=37%).

$^1$H-NMR: 0.87 (3 sharp peaks, 6H), 0.95 (s, 3H), 1.02 (d, 3H, J=7.3), 1.05 (s, 3H), 1.08 (s, 3H), 1.17 (s, 3H), 1.32 (m, 2H), 1.84 (m, 3H), 2.39 (m, 2H). $^{13}$C-NMR: 200.2 (s), 163.2 (s), 139.4 (s), 48.3 (t), 40.8 (d), 40.1 (s), 38.7 (d), 37.0 (s), 36.3 (t), 29.5 (t), 26.4 (q), 25.5 (q), 21.3 (q), 19.8 (q), 19.4 (q), 13.5 (q), 12.8 (q). MS: 248 (83), 233 (100), 205 (36), 191 (76), 177 (82), 163 (46), 149 (19), 135 (18), 121 (21).

Example 2

Synthesis of 3,5,5,6,7,8,8-heptamethyl-3,4,5,6,7,8-hexahydronaphthalen-2(1H)-one a) Synthesis of 1,2,3,4-tetrahydro-1,1,2,3,4,4,6-heptamethylnaphthalene A solution of paracymene (54.0 g, 0.4 mol) in $CH_2Cl_2$ (80 g) was treated with $AlCl_3$ (1.36 g, 10.2 mmol). After stirring for 1 hour, (E)-4,4-dimethyl-2-pentene (20 g, 0.2 mmol) was added at 2° C. in 90 minutes. After 3 hours stirring the reaction mixture was poured, under vigorous stirring, into a ice/water mixture (40 g). The phases were separated and the organic layer washed with water, saturated $NaHCO_3$ water solution and brine. The organic layer was then concentrated to dryness and the crude product was distilled (50-100° C./3 Torr) and then redistilled (70° C./ 0.7 Torr) to afford pure product as a mixture of 84/14 trans/cis isomers with a yield of 30%.

Two NMR and MS spectra of the main isomer were identical to those described for the corresponding trans compound in example 1.a).

b) Synthesis of 1,2,3,4,5,8-hexahydro-1,1,2,3,4,4,6-heptamethylnaphthalene

The desired compound was obtained using 1,2,3,4-tetrahydro- 1,1,2,3,4,4,6-heptamethylnaphthalene and applying the same experimental procedure as described in example 1b).

MS: 232 (20), 217 (10), 133 (82), 119 (100), 105 (31), 91 (35), 55 (32), 41 (42).

c) Synthesis of 2,5,5,6,7,8,8-heptamethyl-1,2,3,4,5,6,7,8-octahydro-2,3-epoxy-naphthalene A mixture of t-butylhydroperoxide (5.5 M in nonane (Fluka); 12.63 ml; 69.5 mmol), $Mo(CO)_6$ (214 mg; 0.8 mmol; 2 mol-%) and 1,2-dichloroethane (38 ml) was heated under $N_2$ at 70° C. for 30 min. The mixture was added at 80° C. in 15 min to a stirred solution of the compound obtained under b) (14.49 g; 65% pure; 40.5 mmol) and $Na_2HPO_4$ (9.42 g; 40.5 mmol) in 1,2-dichloroethane (68 ml). After 2 hours, the cooled reaction mixture was treated with 10% aqueous $Na_2SO_3$ (184 ml) and stirred for 3 hours. After extraction (ether), washing of the organic layer (water, then brine) and drying ($Na_2SO_4$), the crude product was distilled in a bulb-to-bulb oven (0.01 mbar, 100-120° C.) to afford a crude product which was further purified by flash chromatography ($SiO_2$; cyclohexane/ethylacetate 98:2) to afford 4.90 g of the desired epoxide, in the form of a mixture of four diastereomers, (90% pure; yield=44%).

$^1$H-NMR (main isomers): 0.77 (s, 3H), 0.80 (s, 3H), 0.83-0.86 (4 sharp peaks, 6H), 0.93 (s, 3H), 0.98 (2 sharp peaks, 3H), 1.20-1.40 (m, 2H), 1.37 (s, 3H), 2.15-2.80 (m, 4H), 3.07 (br. s, 1H). $^{13}$C-NMR (main isomers): 130.6 (s), 129.4 (s), 58.8 (d), 56.8 (s), 39.4/39.8 (2d), 37.8 (s), 31.0 (t), 26.7 (t), 26.4 (q), 26.3 (q), 22.8 (q), 21.1 (q), 19.6 (q), 14.1 (q), 13.7 (q). MS: 248 (28), 233 (45), 205 (18), 175 (78), 149 (30), 135 (39), 133 (30), 121 (55), 119 (43), 105 (35), 91 (41), 83 (30), 55 (42), 43 (100), 41 (70).

d) Synthesis of 3,5,5,6,7,8,8-heptamethyl-3,4,5,6,7,8-hexahydronaphthalen-2(1H)-one $BF_3.OEt_2$ (1.48 g; 1.30 ml; 10.4 mmol) was added at 3° C. in 3 minutes to a solution of epoxide obtained in example 1) (2.05 g; 80% pure; 6.60 mmol) in $CH_2Cl_2$ (80 ml). The reaction mixture was hydrolyzed with saturated aqueous $NaHCO_3$ (25 ml) and stirred for 1 h. The phases were separated and the products were extracted with ether, washed with water, then saturated aqueous NaCl, dried ($Na_2SO_4$) and concentrated. Bulb-to-bulb distillation (100° C., 0.05 mbar) and flash chromatography ($SiO_2$; cyclohexane/AcOEt=93.7) allowed the isolation of the title compound (673 mg; 90% pure; 37% yield).

$^1$H-NMR (main isomers): 0.78(s, 3H); 0.82(s, 3H); 0.87 (m, 6H); 0.95(s, 3H); 1.03(s, 3H); 1.10(d, J=7,3H); 1.35(m, 2H) ; 2.08(dd, J=15, 8, 1H); 2.23(m, 1H) 2.49(dd, J=15.5, 1H) ; 2.85(d, J=19.1H) ; 2.92(d, J=19, 1H). $^{13}$C-NMR (main isomers): 215.2(s), 136.8(s), 132.6(s), 42.0(d), 40.6(t), 39.9 (d), 39.8(d), 38.0(s), 37.6(s), 32.4(t), 26.0(q), 25.9(q), 20.04 (q), 20.0(q), 15.7(q), 13.7(q), 13.6(q). MS: 248($M^±$, 42), 233(100), 191(23), 177(48), 161(22), 149(24), 123(25), 121 (27).

Example 3

Synthesis of (6RS,7RS)-5,5,6,7,8,8-hexamethyl-3,4,5,6,7,8-hexahydronaphthalen-2(1H)-one a) Synthesis of trans-1,2,3,4-tetrahydro-1,1,2,3,4,4-hexamethyl-6-dibromomethyl-naphthalene A solution of the compound obtained in example 1.a) (39.06 g; 170 mmol) and NBS (72.4 g; 406 mmol) in $CCl_4$ (400 ml) was irradiated with a 160 W lamp and heated at reflux for 90 minutes. The reaction mixture was diluted with 100 ml of ether and washed with water, and the organic layer thus obtained dried and evaporated to provide a crude product 92% pure by GC.

$^1$H-NMR: 0.96(m, 6H); 1.08(s, 3H); 1.10(s, 3H); 1.30(s, 3H), 1.32(s, 3H), 1.56(m, 2H); 6.63(s, 1H); 7.35(2s, 2H); 7.45(s, 1H). $^{13}$C-NMR: 147.7(s), 145.8(s), 138.8(s), 127.8 (d), 125.0(d), 123.8(d), 41.8(d), 39.1(2d), 38.0(2s), 29.4(2q), 25.6(q), 25.5(q), 13.8(2q). MS: 307/309($M^±$—Br, 100/96), 249/251(15).

b) Synthesis of trans-1,2,3,4-tetrahydro-1,1,2,3,4,4-hexamethyl-6-carbaldehyde-naphthalene A solution of the above dibromide (79.7 g), HCOONa (38.55 g; 567 mmol) and EtOH/water 4:1 (1400 ml) was heated at reflux (110° C.) for 90 minutes. After evaporation of EtOH and extraction with ether, the residue was dissolved in MeOH (420 ml), treated with 10% aqueous KOH (185 ml) and heated further for 30 minutes. Evaporation of MeOH at the rotavapor, extraction with ether and bulb-to-bulb distillation (0.01 mbar; 150° C.) afforded 30.8 g of desired aldehyde (yield: 74%).

$^1$H-RMN: 0.97-1.03 (d, 6H, J=7 Hz), 1.13 (s, 3H), 1.14 (s, 3H), 1.34 (s, 3H), 1.37(s, 3H), 1.55-1.65 (m, 2H), 7.49-7.55 (d, 1H, J=7.5 Hz), 7.59-7.67 (dd, 1H, J=1.5 et 7.5 Hz), 7.89 (d, 1H, J=1.5 Hz), 9.96 (s, 1H). $^{13}$C-RMN: 192.30 (d), 153.12 (s), 146.67 (s), 134.16 (s), 129.72 (d), 128.18 (d), 126.08 (d), 39.17 (d), 39.07 (d), 38.60 (s), 38.08 (s), 29.44 (q), 29.28 (q), 25.62 (q), 25.32 (q), 13.83 (q), 13.77 (q). MS: 244 (6), 229 (24), 187 (32), 173 (100), 159 (24), 145 (26), 128 (20), 117 (42), 91 (19), 57 (58), 43 (24).

c) Synthesis of trans-1,2,3,4-tetrahydro-1,1,2,3,4,4-hexamethylnaphthalene

A mixture of the compound obtained under b) (30.8 g; 126 mmol), 10% Pd/C (616 mg; 2% by weight) and $Na_2CO_3$ (940 mg), under $N_2$, was heated in a two-necked flask fitted with a condenser at 175° C. for 21 hours. The cooled solid reaction mixture was dissolved in ether, filtered on CELITE®, concentrated and purified by a bulb-to-bulb distillation (0.01 mbar; 125° C.) to afford the desired naphthalene derivative (purity: 94%; yield=84%).

$^1$H-RMN: 0.96(m, 6H); 1.10(s, 6H); 1.31(s, 6H); 1.59(m, 2H) ; 7.13(m, 2H); 7.35(m, 2H). $^{13}$C-NMR: 145.5(s), 127.1 (d), 125.4(d), 39.2(d), 37.8(s), 29.5(q), 25.6(q), 13.8(q).

MS : 216($M^±$, 40), 201(86), 159(76), 145(100), 128(19), 117(27), 57(39).

d) Synthesis of trans-1,2,3,4,5,8-hexahydro-1,1,2,3,4,4-hexamethylnaphthalene

Methylamine (140 ml) was condensed in a 5-necked flask fitted with a $CO_2$-condenser and an argon line. The temperature was allowed to reach −20° C. and a solution of the compound obtained under c) (10.0 g; 46.3 mmol) in THF (27 ml) and EtOH (8.1 ml) was added. This magnetically stirred solution was treated at −20 to −10° C. portion-wise with lithium (964 mg; 138.9 mmol). After complete addition (30 min), stirring was continued for 5 minutes, then saturated aqueous NH$_4$Cl was added and the products extracted with ether. The organic phase was washed with 5% aqueous HCl, water and then brine to be finally dried (Na$_2$SO$_4$) and evaporated. Bulb-to-bulb distillation (0.01 mbar, 120° C.) afforded the title compound (yield=45%).

$^1$H-RMN: 0.83(s, 6H); 0.87(m, 6H); 0.98(s, 6H); 1.39(m, 2H); 2.55-2.80(m, 4H); 5.76(br.s, 2H). $^{13}$C-NMR: 132.8(s), 124.9(d), 39.7(d), 37.8(s), 26.6(t), 26.10(q), 20.3(q), 13.9 (q).

MS : 218(M$^±$, 65), 203(100), 175(18), 161(34), 147(52), 119(77), 105(76), 91(39).

e) Synthesis of (6RS, 7RS)-5,5,6,7,8,8-hexamethyl-3,4,5,6,7,8-hexahydronaphthalen-2(1H)-ol A solution of the compound obtained under d) (48.2 mmol) in THF (200 ml) was cooled at 0° C. and treated dropwise with BH$_3$Me$_2$S (36.2 mmol). After stirring for 70 minutes, was added NaOH (72.2 mmol) dissolved in water (30 ml), and finally were added 12 ml of 35% H$_2$O$_2$. The reaction mixture stirred for 1 hours at room temperature and then extracted with ether. Then, organic layer was washed with water, saturated NaHCO$_3$ water solution and then brine to be finally dried (Na$_2$SO$_4$) and evaporated. The alcohol was obtained as 1/1 mixture of two diastereoisomers and was not purified any further. MS : 236(M$^±$, 36), 221(100), 203(95), 161(73), 147(67).

f) Synthesis of (6RS, 7RS)-5,5,6,7,8,8-hexamethyl-3,4,5,6,7,8-hexahydronaphthalen-2(1H)-one A solution of the compound obtained under e) (23.8 mmol) in acetone (220 ml) was cooled at 0° C. and treated with Jones reagent (47.5 mmol). After complete addition, brine (200 ml) was added to the reaction mixture. The product was extracted with pentane and washed with water, saturated NaHCO$_3$ water solution and then brine to be finally dried (Na$_2$SO$_4$) and evaporated. A distillation (0.01 Torr; 100° C.) afforded a crude product which was further purified by a chromatography (SiO$_2$; cyclohexane/AcOEt=98:2) to obtain the desired ketone (yield: 47% for the last two steps).

$^1$H-RMN: 0.78(s, 3H); 0.83(s, 3H) ; 0.88(m, 6H); 0.96(s, 3H); 1.01(s, 3H); 1.35(m, 2H); 2.26(m, 2H); 2.37(m, 2H); 2.82(d, 1H, J=18); 2.96(d, 1H, J=18). $^{13}$C-NMR : 213.6(s), 138.2(s), 133.1(s), 41.6(t), 39.8(2d), 38.3(t), 38.3(s), 37.7(s), 26.1(q), 25.6(q), 24.6(t), 20.1(q), 20.0(q), 13.6(2q). MS: 234(M$^±$, 41), 19(100), 177(26), 163(55), 123(34), 121(38).

Example 4

Synthesis of (4aRS,6RS,7RS,8aSR)-5,5,6,7,8,8-hexamethylhexahydro-4a,8a-epoxynaphthalen-1 (2H)-one, (6RS,7RS)-5,5,6,7,8,8-hexamethyl-3,4,5,6,7,8-hexahydronaphthalen-1(2H)-one, (4aSR,6RS,7RS,8aRS)-5,5,6,7,8,8-hexamethylhexahydro-4a, 8a-epoxynaphthalen-1(2H)-one and (6RS,7RS)-5,5, 6,7,8,8-hexamethyl-4,4a,5,6,7,8-hexahydronaphthalen-2(3H)-one a) Synthesis of a mixture of (2RS,3RS)-1,1,2,3,4,4-hexamethyl-1,2,3,4,5,6,7,8-octahydronaphthalene and (2RS,3RS)-1,1,2,3,4,4-hexamethyl-1,2,3,4,6,7,8, 8A-octahydronaphthalene 140 ml of methylamine were condensed in a 5-necked flask fitted with a CO$_2$-condenser and an argon line. The temperature was allowed to reach −20° C. and a solution of the compound obtained under Example 3.c) (10.0 g; 46.3 mmol) in THF (27 ml) and EtOH (8.1 ml) was added. This magnetically stirred solution was treated at −20 to −10° C. portion-wise with lithium (964 mg; 138.9 mmol). After complete addition (30 min), stirring was continued for 1 h, then additional lithium (964 mg; 138.9 mmol) was added to the decolorized suspension and stirring continued for 1 hour. Saturated aqueous NH$_4$Cl was added and the products extracted with ether. The organic phase was washed with 5% aqueous HCl, water, then brine, dried (Na$_2$SO$_4$) and evaporated (9.78 g). Bulb-to-bulb distillation (0.01 mbar, 120° C.) afforded 9.35 g of a mixture of (2RS,3RS)-1,1,2,3,4,4-Hexamethyl-1,2,3,4,5,6,7,8-octahydronaphthalene (65% by GC) and (2RS,3RS)-1,1,2,3,4,4-Hexamethyl-1,2,3,4,6,7,8, 8A-octahydronaphthalene (26% by GC). (2RS,3RS)-1,1,2, 3,4,4-Hexamethyl-1,2,3,4,5,6,7,8-octahydronaphthalene:

$^1$H-NMR: 0.78(s, 6H); 0.84(m, 6H); 0.93(s, 6H); 1.24-1.37(m, 4H); 1.74(m, 2H); 1.88-2.07(m, 4H). $^{13}$C-NMR: 134.6(s), 39.7(d), 38.1(s), 25.8(t), 25.8(q), 23.8(t), 20.4(q), 13.7(q). MS: 220(M$^±$, 36),205(100), 163(43), 149(52), 137 (19), 123(33). (2RS,3RS)-1,1,2,3,4,4-Hexamethyl-1,2,3,4,6, 7,8,8A-octahydronaphthalene: MS: 220(M$^±$, 38), 205(100), 163(28), 149(37), 135(25), 123(62), 122(54), 107(33).

b) Synthesis of (2RS,3RS)-1,1,2,3,4,4-hexamethyl-1,2,3,4,5,6,7,8-octahydronaphthalene 140 ml of methylamine were condensed in a 5-necked flask fitted with a CO$_2$-condenser and an argon line. The temperature was allowed to reach −20° C. and a solution of the compound obtained under Example 3.c) (10.0 g; 46.3 mmol) in THF (27 ml) and EtOH (8.1 ml) was added. This magnetically stirred solution was treated at −20 to −10° C. portion-wise with lithium (964 mg; 138.9 mmol). After complete addition (30 min), stirring was continued for 5 minutes, then saturated aqueous NH$_4$Cl was added and the products extracted with ether. The organic phase was washed with 5% aqueous HCl, water, then brine, dried (Na$_2$SO$_4$) and evaporated (9.82 g). Bulb-to-bulb distillation (0.01 mbar, 120° C.) afforded a mixture containing (2RS, 3RS)-1,1,2,3,4,4-hexamethyl-1,2,3,4,5,8-hexahydronaphthalene (50% by GC), (2RS,3RS)-1,1,2,3,4,4-hexamethyl-1,2,3,4,5,6,7,8-octahydronaphthalene (29% by GC) and the starting compound (20% by GC). This mixture was hydrogenated with 10% Pd/C (230 mg) in toluene. The final crude product was bulb-to-bulb distilled to obtain a mixture containing (2RS,3RS)-1,1,2,3,4,4-hexamethyl-1,2,3,4,5,6,7,8-octahydronaphthalene (74% by GC), the starting compound (20% by GC) and the isomer (2RS,3RS)-1,1,2,3,4,4-hexamethyl-1,2,3,4,6,7,8,8A-octahydronaphthalene (6% by GC).

c) Synthesis of (6RS,7RS)-5,5,6,7,8,8-hexamethyl-3,4,5,6,7,8-hexahydronaphthalen-1(2H)-one and (6RS,7RS)-5,5,6,7,8,8-hexamethyl-4,4a,5,6,7,8-hexahydronaphthalen-2(3H)-one A suspension of CrO$_3$ (46.9 g; 469 mmol) in CH$_2$Cl$_2$ (500 ml) was cooled at −20° C. and treated at once with 3,5-dimethylpyrazole (DMP) (45.0 g; 469 mmol). After 20 minutes, the dark violet solution was treated dropwise (1 h) with a solution of the mixture obtained under a) (7.59 g; 34.5 mmol) in CH$_2$Cl$_2$ (400 ml). After stirring at −20° C. for 1 hour, aqueous 6 M NaOH (100 ml) was added and the solution stirred at 0° C. for 30 min. More water was then added and phases separated. The CH$_2$Cl$_2$ phase was washed with aqueous 5% HCl, brine (3 times), dried (Na$_2$SO$_4$) and evaporated. The concentrate was bulb-to-bulb distilled (0.01 mbar; 150-160° C.) to afford of a solid distillate containing DMP and a residue. Recrystallization from toluene allowed to recover DMP and a mother liquors which still contained DMP. This was removed by selective bulb-to-bulb distillation (1 mbar; 100° C.). The residue was purified by flash chromatography (SiO$_2$, cyclohexane/ethylacetate 98:2).

The following products were obtained: (6RS,7RS)-5,5,6,7,8,8-hexamethyl-3,4,5,6,7,8-hexahydronaphthalen-1(2H)-one (90% pure; yield=24%): $^1$H-NMR: 0.86(3 sharp peaks, 6H); 0.94(s, 3H); 1.05(s, 3H); 1.10(s, 3H); 1.16(s, 3H); 1.32(m, 2H); 1.65(m, 1H); 1.91(m, 1H); 2.08-2.26(m, 2H); 2.37-2.47(m, 2H). $^{13}$C-NMR: 199.9(s), 163.8(s), 139.8(s), 40.7(d), 40.3(t), 40.2(s), 38.8(d), 37.1(s), 27.6(t), 26.4(q), 25.6(q), 22.5(t), 19.8(q), 19.5(q), 13.5(q), 12.8(q). MS: 234(M$^+$, 66), 219(67), 191(42), 177(77), 163(100), 149(43), 135(31), 121(35), 91(37), 55(45), 41(47). (6RS,7RS)-5,5,6,7,8,8-hexamethyl-4,4a,5,6,7,8-hexahydronaphthalen-2(3H)-one (91% pure; yield=55%): $^1$H-NMR: 0.65(s, 3H); 0.88(d, J=7, 3H); 0.93(d, J=7,3H); 1.00(s, 3H); 1.06(s, 3H); 1.15(s, 3H); 1.23-1.42(m, 2H); 1.95(m, 1H); 2.07(m, 1H); 2.23(m, 1H); 2.40(m, 2H); 6.10(d, J=1.5, 1H). $^{13}$C-NMR: 200.9(s), 173.9(s), 123.0(d), 44.2(d), 44.0(d), 42.7(d), 40.8(s), 40.6(s), 35.7(t), 26.7(q), 25.6(q), 23.1(q), 22.0(t), 15.3(q), 14.5(q), 13.8(q). MS: 234(M$^+$, 19), 177(18), 164(22), 149(36), 138(75), 136(51), 121(23), 107(22), 97(100), 93(23).

d) Synthesis of (6RS,7RS)-5,5,6,7,8,8-hexamethyl-3,4,5,6,7,8-hexahydronaphthalen-1(2H)-one, (4aRS,6RS,7RS,8aSR)-5,5,6,7,8,8-hexamethylhexahydro-4a,8a-epoxynaphthalen-1(2H)-one and (4aSR,6RS,7RS,8aRS)-5,5,6,7,8,8-hexamethylhexahydro-4a,8a-epoxynaphthalen-1(2H)-one A suspension of CrO$_3$ (52.9 g; 529 mmol) in CH$_2$Cl$_2$ (500 ml) was cooled at −20° C. and treated at once with 3,5-dimethylpyrazole (DMP) (50.7 g; 528 mmol). After 20 min, the dark violet solution was treated dropwise (1 h) with a solution of (2RS,3RS)-1,1,2,3,4,4-Hexamethyl-1,2,3,4,5,6,7,8-octahydronaphthalene obtained under b) (8.75 g; 74% pure) (29.4 mmol) in CH$_2$Cl$_2$ (400 ml). After stirring at −20° C. for 4 hours, aqueous 6 M NaOH (250 ml) was added and the product extracted as in c). The residue was purified by flash chromatography (SiO$_2$; using cyclohexane/ethylacetate 98:2).

The following products were obtained: (6RS,7RS)-5,5,6,7,8,8-hexamethyl-3,4,5,6,7,8-hexahydronaphthalen-1(2H)-one (yield=25%): having the same NMR spectra as described above. (4aRS,6RS,7RS,8aSR)-5,5,6,7,8,8-hexamethylhexahydro-4a,8a-epoxynaphthalen-1(2H)-one (yield=14%): $^1$H-NMR: 0.72(d, J=7,3H); 0.75(d, J=7,3H); 0.91(s, 3H); 1.04(s, 3H); 1.14(s, 3H); 1.16(s, 3H); 1.18(m, 1H); 1,43(m, 1H); 1.54(m, 1H); 1.77-1.97(m, 2H) 2.06(m, 1H); 2.16(m, 1H); 2.50(m, 1H). $^{13}$C-NMR: 208.3(s), 73.4(s), 73.1(s), 38.9(d), 38.6(t), 36.9(d), 36.5(s), 35.6(s), 25.6(q), 25.4(t), 23.4(q), 18.0(q), 16.8(q), 16.6(t), 13.8(q), 12.1(q). MS: 235(43), 154(44), 137(45), 125(80), 109(33), 97(71), 83(41), 67(42), 55(94), 43(100), 41(90). (4aSR,6RS,7RS,8aRS)-5,5,6,7,8,8-hexamethylhexahydro-4a,8a-epoxynaphthalen-1(2H)-one (yield=5%): $^1$H-NMR: 0.73(d, J=7,3H); 0.75(d, J=7,3H);0.92(s, 3H); 1.08(s, 6H); 1.10(m, 1H); 1.12(s, 3H); 1.43(m, 1H); 1.65(m, 2H); 1.92-2.03(m, 2H); 2.18(m, 1H); 2.39(m, 1H). $^{13}$C-NMR: 203.9(s), 72.2(s), 69.9(s), 40.3(t), 40.0(d), 38.1(s), 35.4(d), 33.6(s), 25.5 (q), 24.8(t), 23.6(q), 17.9(q), 17.9(t), 17.6(q). 13.1(q), 13.0(q). MS: 235(50), 207(63), 179(36), 137(61), 125(100), 109(34), 97(63), 55(58), 43(61).

Example 5

Preparation of a Perfuming Composition

An eau de toilette for man, having a floral, woody and herbal character, was prepared by admixing the following ingredients:

| Ingredient | Parts by weight |
| --- | --- |
| Benzyl acetate | 10 |
| Bornyl acetate | 10 |
| Linalyl acetate | 450 |
| 10%* C10 aldehyde | 20 |
| 10%* MNA aldehyde | 10 |
| 10%* Allyl Amyl Glycolate | 60 |
| AMBROX ®[1] | 10 |
| Aspic essential oil | 20 |
| Bergamote Abergapt | 400 |
| 10%* Cardamom essential oil | 50 |
| Citral | 10 |
| Citronellol | 70 |
| 4-Cyclohexyl-2-methyl-2-butanol[2] | 150 |
| Coumarine 10% DIPG | 50 |
| CYCLOGALBANATE ®[3] | 15 |
| (1'R,E)-2-Ethyl-4-(2',2',3'-trimethyl-3'-cyclopenten-1'-yl)-2-buten-1-ol | 20 |
| 1%* Delta Damascone | 30 |
| Dihydromyrcenol | 120 |
| Eugenol | 20 |
| 10%* Galbanum essential oil | 10 |
| Geranium China essential oil | 30 |
| HEDIONE ®[4] HC | 400 |
| 3-(1,3-Benzodioxol-5-yl)-2-methylpropanal[2] | 20 |
| IRALIA ®[5] | 30 |
| ISO E SUPER ®[6] | 200 |
| Lavandin Grosso essential oil | 10 |
| 10%* Liffarome[7] | 25 |
| Linalool | 400 |
| LYRAL ®[8] | 40 |
| Mandarine essential oil | 30 |
| 10%* Crystalmoss | 30 |
| Patchouli | 130 |
| POLYSANTOL ®[9] | 40 |
| Portugal Bresil essential oil | 90 |
| Benzyl salicylate | 50 |
| Santal essential oil | 70 |
| 10%* 5-Methyl-3-heptanone-oxime[10] | 30 |
| 10%* 2,4-Dimethyl-3-cyclohexen-1-carboxaldehyde | 40 |
| 10%* Vanilline | 10 |
| VERDOX ®[11] | 20 |
| VERTOFIX ®[12] | 170 |
| | 3400 |

*in dipropyleneglycol
[1] (−)-(8R)-8,12-Epoxy-13,14,15,16-tetranorlabdane; origin: Firmenich, Switzerland
[2] Origin: Firmenich, Switzerland
[3] Allyl (cyclohexyloxy)-acetate; origin: Dragoco, Germany
[4] High cis methyl dihydrojasmonate; origin: Firmenich, Switzerland
[5] Mixture of methylionones isomers; origin: Firmenich, Switzerland
[6] 1-(Octahydro-2,3,8,8-tetramethyl-2-naphthalenyl)-1-ethanone; origin: I.F.F., Switzerland
[7] 3-Hexenyl-methyl carbonate; origin: I.F.F., Switzerland
[8] 4/3-(4-Hydroxy-4-methylpentyl)-3-cyclohexene-1-carbaldehyde; origin: I.F.F., Switzerland
[9] 3,3-Dimethyl-5-(2,2,3-trimethyl-3-cyclopenten-1-yl)-4-penten-2-ol; origin: Firmenich, Switzerland
[10] Origin: Givaudan SA, Switzerland
[11] 2-Tert-butyl-1-cyclohexyl acetate; origin: I.F.F., Switzerland
[12] Origin: International Flavors & Fragrances, USA The addition of 100 parts by weight of (6RS,7RS)-5,5,6,7,8,8-hexamethyl-3,4,5,6,7,8-hexahydronaphthalen-1(2H)-one to the above-described eau de toilette imparted to the latter a powerful musky and earthy connotation, having also a well appreciated aspect which is slightly ambrette and pine. The overall effect was in-between the one which could have been brought by the addition of CASHMERAN® or TONALIDE®, however the substantivity was by far superior to that which could have been imparted by the addition of CASHMERAN®, and its musky-ambrette character was more elegant than the one provided by TONALIDE®. The addition of (6RS,7RS)-3,5,5,6,7,8,8-heptamethyl-3,4,5,6,7,8-hexahydronaphthalen-1(2H)-one or (6RS,7RS)-5,5,6,7,8,8-hexamethyl-3,4,5,6,7,8-hexahydronaphthalen-2(1H)-one, instead of (6RS,7RS)-5,5,6,7,8,8-hexamethyl-3,4,5,6,7,8-hexahydronaphthalen-1(2H)-one, to the above-described eau de toilette provided a more classic fragrance, wherein the earthy-woody effect was more pronounced than the one which could have been obtained by the addition of TONALIDE®.

Finally, the addition of the same amount of (4aRS,6RS,7RS,8aSR)-5,5,6,7,8,8-hexamethylhexahydro-4a,8a-epoxynaphthalen-1(2H)-one to the eau de toilette described above imparted a character which was much more powdery, almost nitro-musk, compared to the one obtained by the addition of (6RS,7RS)-5,5,6,7,8,8-hexamethyl-3,4,5,6,7,8-hexahydronaphthalen-1(2H)-one.

Example 6

Preparation of a Perfuming Composition

A perfuming base for a detergent, having a floral and powdery character, was prepared by admixing the following ingredients:

| Ingredient | Parts by weight |
|---|---|
| Hexylcinnamic aldehyde | 800 |
| Methyl anthranilate | 10 |
| CETALOX ®[1)] | 10 |
| Citronellol | 50 |
| 4-Cyclohexyl-2-methyl-2-butanol[2)] | 40 |
| HEDIONE ®[3)] | 100 |
| HIVERNAL ®[4)] | 10 |
| 10%* Indol | 10 |
| IRALIA ®[5)] total | 100 |
| LILIAL ®[6)] | 70 |
| Terpineol | 30 |
| VERTOFIX ®[7)] | 70 |
| | 1300 |

*in dipropyleneglycol
[1)]8,12-Epoxy-13,14,15,16-tetranorlabdane; origin: Firmenich, Switzerland
[2)]Origin: Firmenich, Switzerland
[3)]Methyl dihydrojasmonate; origin: Firmenich, Switzerland
[4)]3-(3,3/1,1-Dimethyl-5-indanyl)propanal; origin: Firmenich, Switzerland
[5)]Mixture of methylionones isomers; origin: Firmenich, Switzerland
[6)]3-(4-Tert-butylphenyl)-2-methylpropanal; origin: Givaudan SA, Switzerland
[7)]Origin: International Flavors & Fragrances, USA The addition of 1200 parts by weight of (6RS,7RS)-5,5,6,7,8,8-hexamethyl-3,4,5,6,7,8-hexahydronaphthalen-1(2H)-one to the above-described perfuming base provoked, in the fragrance of the latter, the bursting of a musky, ambery and balsamic symphony, accompanied by an astonishing warm and sweetness.

However, if there was added to the base the same amount of (6RS,7RS)-3,5,5,6,7,8,8-heptamethyl-3,4,5,6,7,8-hexahydronaphthalen-1(2H)-one or (6RS,7RS)-5,5,6,7,8,8-hexamethyl-3,4,5,6,7,8-hexahydronaphthalen-2(1H)-one the whole olfactif effect was closer to the one provided by Tonalide®. The effect obtained by the addition of (6RS,7RS)-5,5,6,7,8,8-hexamethyl-3,4,5,6,7,8-hexahydronaphthalen-2(1H)-one was also slightly more ambrette than the one imparted by (6RS,7RS)-3,5,5,6,7,8,8-heptamethyl-3,4,5,6,7,8-hexahydronaphthalen-1(2H)-one.

If instead of the above-mentioned invention compounds there was added (4aRS,6RS,7RS,8aSR)-5,5,6,7,8,8-hexamethylhexahydro-4a,8a-epoxynaphthalen-1(2H)-one, the effect imparted was very similar to the one which could have been provided by the perfuming ingredient known as Musk Ambrette.

What is claimed is:

1. A compound of formula (I) or (I') having musky and earthy odor characteristics

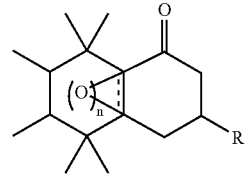
(I)

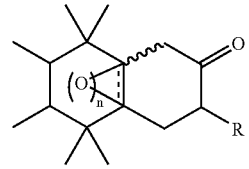
(I')

wherein R represents a hydrogen atom or a methyl group, and
  a) in formula (I):
    n is 1 and the dotted line represents a single bond; or
    n is 0 and the dotted line represents a double bond; or
  b) in formula (I'):
    n is 0, the wavy line indicates a double bond and the dotted line a single bond; or
    n is 0, the wavy line indicates a single bond, the dotted line a double bond; or
    n is 1, the wavy line indicates a single bond, the dotted line a single bond.

2. As a compound of claim 1, a compound of formula (II) or (II')

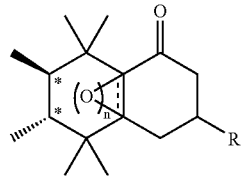
(II)

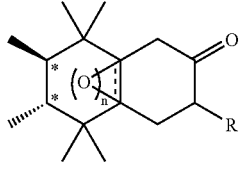
(II')

wherein
- the two methyl groups bonded to the carbons marked by an asterisk possess a trans configuration;
- R represents a hydrogen atom or a methyl group; and
- n is 1 and the dotted line represents a single bond or n is 0 and the dotted line represents a double bond.

3. As a compound according to claim 1, (6RS,7RS)-5,5,6,7,8,8-hexamethyl-3,4,5,6,7,8-hexahydronaphthalen-1(2H)-one, (6RS,7RS)-3,5,5,6,7,8,8-heptamethyl-3,4,5,6,7,8-hexahydronaphthalen-1(2H)-one, (4aRS,6RS,7RS,8aSR)-5,5,6,7,8,8-hexamethylhexahydro-4a,8aepoxynaphthalen-1(2H)-one, (4aSR,6RS,7RS,8aRS)-5,5,6,7,8,8-hexamethylhexahydro-4a,8a-epoxynaphthalen-1(2H)-one, (6RS,7RS)-5,5,6,7,8,8-hexamethyl-4,4a,5,6,7,8-hexahydronaphthalen-2(3H)-one, 3,5,5,6,7,8,8-heptamethyl-3,4,5,6,7,8-hexahydronaphthalen-2(1H)-one or (6RS,7RS)-5,5,6,7,8,8-hexamethyl-3,4,5,6,7,8-hexahydronaphthalen-2(1H)-one.

4. As a compound according to claim 1, (6RS,7RS)-5,5,6,7,8,8-hexamethyl-3,4,5,6,7,8-hexahydronaphthalen-1(2H)-one.

5. A perfuming composition having musky and earthy odor characteristics comprising:
   i) as perfuming ingredient, at least a compound of formula (I) and/or (I'), as defined in claim 1;
   ii) at least one ingredient selected from the group consisting of a perfumery carrier and a perfumery base; and
   iii) optionally at least one perfumery adjuvant.

6. A perfumed article having musky and earthy odor characteristics comprising:
   i) as perfuming ingredient, at least one compound of formula (I) and/or (I'), as defined in claim 1; and
   ii) a consumer product base.

7. A perfumed article according to claim 6, characterized in that the consumer product base is a solid or liquid detergent, a fabric softener, a perfume, a cologne or aftershave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

8. A method to confer, enhance, improve or modify the musky and earthy odor properties of a perfuming composition or of a perfumed article, which method comprises adding to the composition or article an effective amount of at least a compound of formula (I) and/or (I'), as defined in claim 1 to achieve said odor properties.

9. A method to confer, enhance, improve or modify the musky and earthy odor properties of a perfuming composition or of a perfumed article, which method comprises adding to the composition or article an effective amount of at least a compound as defined in claim 2 to achieve said odor properties.

10. A method to confer, enhance, improve or modify the musky and earthy odor properties of a perfuming composition or of a perfumed article, which method comprises adding to the composition or article an effective amount of at least a compound as defined in claim 3 to achieve said odor properties.

11. A method to confer, enhance, improve or modify the musky and earthy odor properties of a perfuming composition or of a perfumed article, which method comprises adding to the composition or article an effective amount of at least a compound as defined in claim 4 to achieve said odor properties.

* * * * *

UNITED STATES PATENT AND TRADEMARK OFFICE
CERTIFICATE OF CORRECTION

PATENT NO.        : 7,253,141 B2                                              Page 1 of 1
APPLICATION NO.   : 11/413456
DATED             : August 7, 2007
INVENTOR(S)       : Fehr It is certified that error appears in the above-identified patent and that said Letters Patent is hereby corrected as shown below:

Column 17
Line 11 (claim 3, line 5), after "5,5,6,7,8,8-hexamethylhexahydro-4a," change "8aepoxynaphthalen-1" to --8a-epoxynaphthalen-1--.

Signed and Sealed this

Thirtieth Day of October, 2007

JON W. DUDAS
*Director of the United States Patent and Trademark Office*